US009471751B1

(12) United States Patent
Kahn et al.

(10) Patent No.: US 9,471,751 B1
(45) Date of Patent: Oct. 18, 2016

(54) TELEMEDICINE SYSTEM FOR PRELIMINARY REMOTE DIAGNOSIS OF A PATIENT

(75) Inventors: Philippe Kahn, Aptos, CA (US); Arthur Kinsolving, Santa Cruz, CA (US)

(73) Assignee: DP Technologies, Inc., Scotts Valley, CA (US)

(*) Notice: Subject to any disclaimer, the term of this patent is extended or adjusted under 35 U.S.C. 154(b) by 679 days.

(21) Appl. No.: 11/682,236

(22) Filed: Mar. 5, 2007

Related U.S. Application Data

(60) Provisional application No. 60/778,765, filed on Mar. 3, 2006.

(51) Int. Cl.
*G06F 19/00* (2011.01)
*G06F 17/30* (2006.01)

(52) U.S. Cl.
CPC ..... *G06F 19/3418* (2013.01); *G06F 17/30699* (2013.01); *G06F 19/322* (2013.01)

(58) Field of Classification Search
CPC ............ G06F 19/322; G06F 19/3418; G06F 19/3406; G06F 17/30
USPC ......................................... 707/706, 649, 661
See application file for complete search history.

(56) References Cited

U.S. PATENT DOCUMENTS

| | | | |
|---|---|---|---|
| 7,359,748 B1* | 4/2008 | Drugge ................ | A61B 5/0064 600/476 |
| 7,412,396 B1* | 8/2008 | Haq ................................. | 705/2 |
| 2001/0037056 A1* | 11/2001 | Nunome ........................ | 600/300 |
| 2002/0049684 A1* | 4/2002 | Nagamoto et al. ................ | 706/1 |
| 2004/0017475 A1* | 1/2004 | Akers et al. ................ | 348/207.1 |
| 2004/0153343 A1* | 8/2004 | Gotlib et al. ...................... | 705/3 |
| 2004/0171955 A1* | 9/2004 | Morganroth .................. | 600/509 |
| 2005/0043969 A1* | 2/2005 | Sarel ................................. | 705/2 |
| 2005/0065813 A1* | 3/2005 | Mishelevich et al. ............ | 705/2 |
| 2005/0283385 A1* | 12/2005 | Hunkeler .............. | G06F 19/324 705/2 |
| 2006/0064319 A1* | 3/2006 | Loevner .................. | G06Q 50/22 705/2 |
| 2006/0074722 A1* | 4/2006 | Chu .................................. | 705/3 |
| 2006/0161456 A1* | 7/2006 | Baker et al. ...................... | 705/2 |
| 2007/0136095 A1* | 6/2007 | Weinstein ......................... | 705/2 |

OTHER PUBLICATIONS

L. E. Graham, Telemedicine—the way adhead for medicine in the developing world, Jan. 2003, Tropical Doctor, vol. 33, pp. 36-38.*

* cited by examiner

*Primary Examiner* — Scott A Waldron
*Assistant Examiner* — Fatima Mina
(74) *Attorney, Agent, or Firm* — HIPLegal LLP; Judith Szepesi

(57) ABSTRACT

A telemedicine system to enable remote pre-diagnosis based on one or more messages from a user is described. The telemedicine system includes a user interface to enable a user to generate a telemedicine query requesting a preliminary diagnosis of a medical condition. The system targets the telemedicine query to an appropriate responder and stores the telemedicine query and any follow-up messages sent in response to the telemedicine query.

24 Claims, 7 Drawing Sheets

TELEMEDICINE SYSTEM FOR PRELIMINARY REMOTE DIAGNOSIS OF A PATIENT

RELATED CASES

The present application claims priority to U.S. Provisional Patent Application Ser. No. 60/778,765, filed Mar. 3, 2006.

FIELD OF THE INVENTION

The present invention relates to telemedicine, and more particularly to enabling a user to communicate health information.

BACKGROUND

Generally speaking when a patient experiences symptoms that cause concern, he or she is prompted to visit a doctor or hospital. However, hospital and doctor visits are usually expensive, and hospital environments are often not the healthiest places.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The method and apparatus described is for providing communication with one or more medical providers or expert systems to provide a preliminary diagnosis of a medical condition based on one or more messages from a user. Remote diagnosis, or telemedicine, provides a method for a user to receive a preliminary diagnosis of various ailments without visiting a special location such as a doctor's office, hospital, or expert system. The data from the user, in one embodiment, includes media data such as images, video, recordings, or other such data.

As camera phones become more ubiquitous and camera resolutions increase, more and more diagnoses may be made remotely based on data received from a user. Alternatively, the user may utilize a standard digital camera—or a film-based system with subsequent digitalization—and then send the message via a computer or other messaging system.

The concept is to enable a user to send a query to one or more medical care providers (which may include doctors, hospitals, insurance companies, and others). The query may include media data, such as one or more images/recordings/video, as well as medical record data in any format. The query may also include a title and a patient identifier. In one embodiment, the title is a patient identifier. In one embodiment, the patient identifier may be a random number shared between the patient (or patients device) and the database. This enables some additional security, as the patient is not identified by name, so if the query is intercepted, it is less likely to be a problem.

Figure 1:
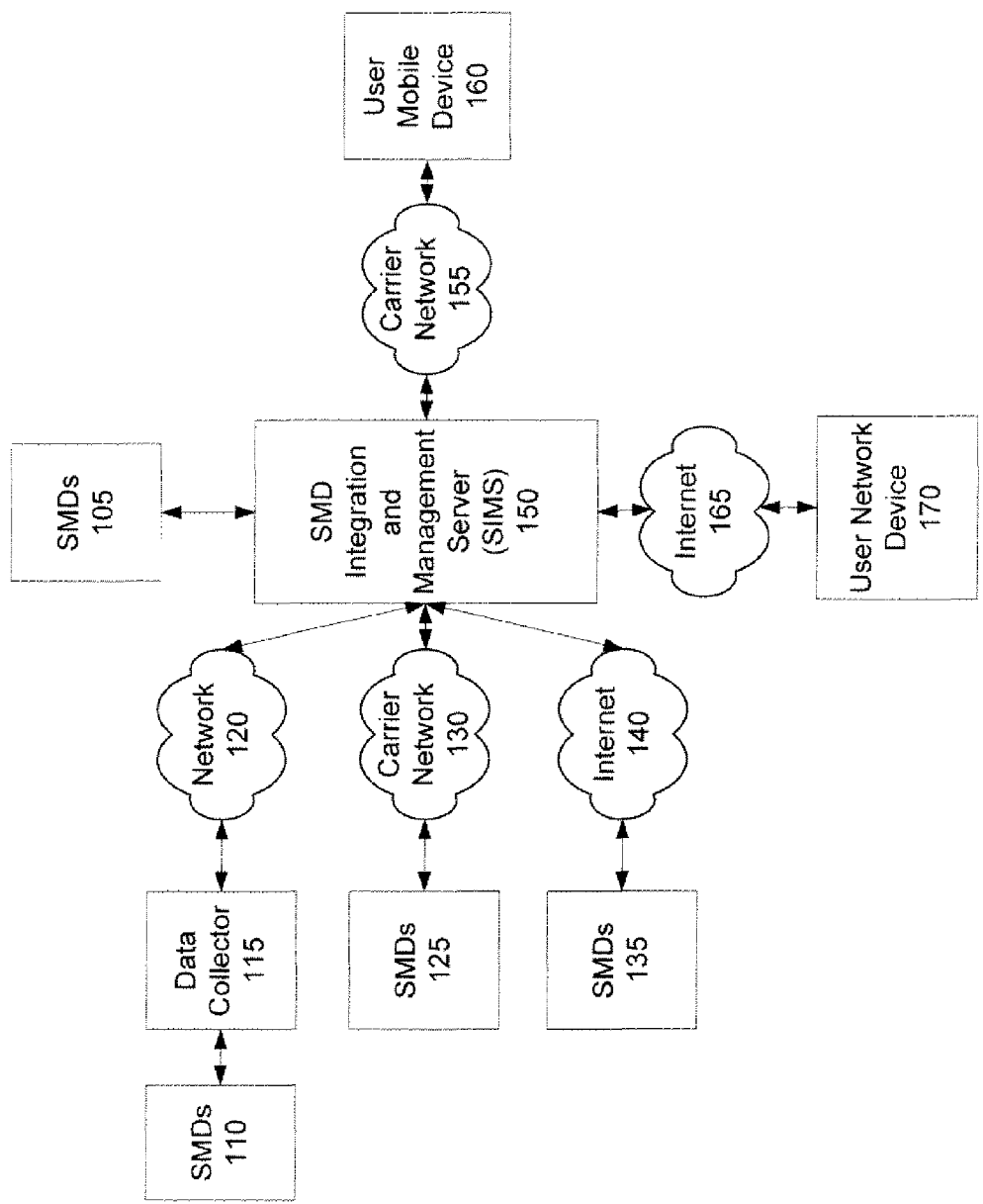
FIG. 1 is a block diagram of one embodiment of a network diagram including an SMD Integration and Management Server (SIMS).

FIG. 1 is a network diagram of one embodiment of the various elements of the system. The various SMDs 105, 110, 125, and 135 are coupled through various means to the SMD Integration and Management Server (SIMS) 150. They may be coupled directly, coupled through carrier network 130, coupled through the Internet 140, or they may be coupled through a data collector 115, which accumulates data from sensor 110, and sends it through network 120, 130, or 140 to SIMS 150. In another embodiment, SMDs may be independent devices which are not coupled to the SIMS 150. Rather, the SIMS 150 may receive data from a user 170 via a network 165. The network may be the Internet 140, a carrier network 130, or any other network. In one embodiment, the SIMS 150 includes a web server, which enables the user to access certain user interface pages, to enter, read, share, and otherwise interact with the collected data.

The data accumulated by SIMS 150 may be available to the user via a user mobile device 160, which accesses SIMS 150 through carrier network 155 or another network, or via another user device 170, such as a computer.

Figure 2:
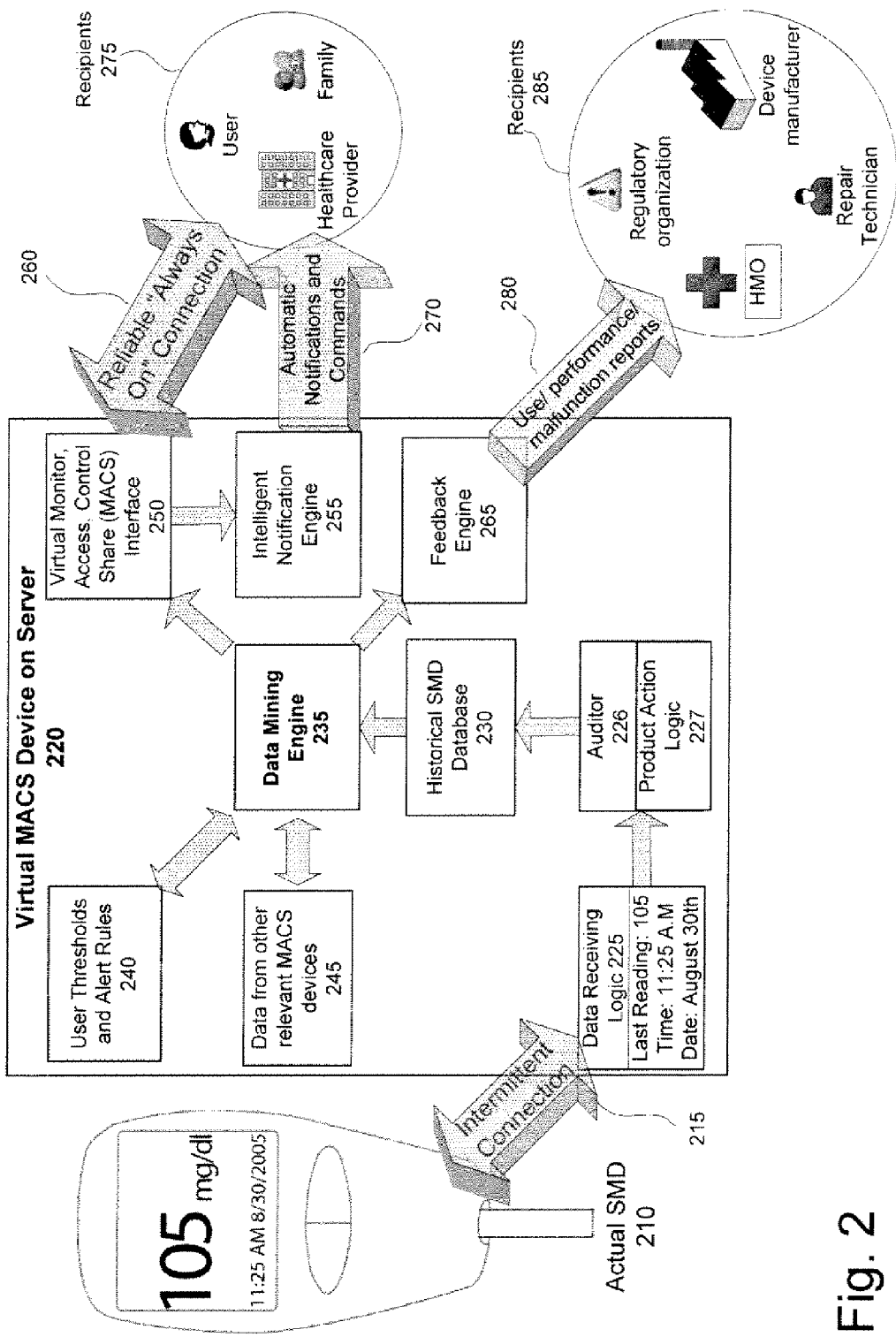
FIG. 2 is a block diagram of a virtual MACS device on the SIMS.

FIG. 2 is a block diagram illustrating one embodiment of a Virtual Management, Access, Control, Share (MACS) device on the SIMS server and its relationship to the actual SMD. The actual SMD 210 has an intermittent connection 215 to a server 220. The connection 215 may be through the Internet, through a carrier network, or through other means. The server 220 may be located in the same location as the real SMD 210.

The data receiving logic 225 receives the data from the actual SMD 210 or the user via an intermittent connection 215. The data is stored in historical database 230. The historical data is used by data mining engine 235, to present virtual MACS device 250 via a reliable always-on connection 260 to various recipients 275. In a healthcare setting for example, the recipients may include the user, healthcare providers, and family.

In one embodiment, data mining engine 235 may further interface with user alerts and rules 240 to generate notifications through intelligent notification engine 255. Intelligent notification engine 255 can send automatic notifications to designated recipients 275, when certain threshold or alert conditions are met. The threshold or alert conditions may include historical data, trend analysis, variance from charted trends, simple threshold, or any combination of the use of historical and current data from the actual SMD 210, or combination of SMDs. In one embodiment, the data mining engine 235 constantly monitors the database 230, to ensure that the alert rules and user thresholds 240 have not been triggered. Intelligent notification engine 255 can, in one embodiment, trigger a notification in an appropriate format to any designated recipient.

In one embodiment, in addition to the database 230, data from other relevant actual SMDs may be received as well via logic 245. For example, in health setting, in addition to the glucose meter, exercise data, medical reports, and/or other relevant conditions may be monitored. The threshold and alert rules 240 may utilize a combination of data from more than one real SMD to trigger a notification or command 270.

Figure 6:
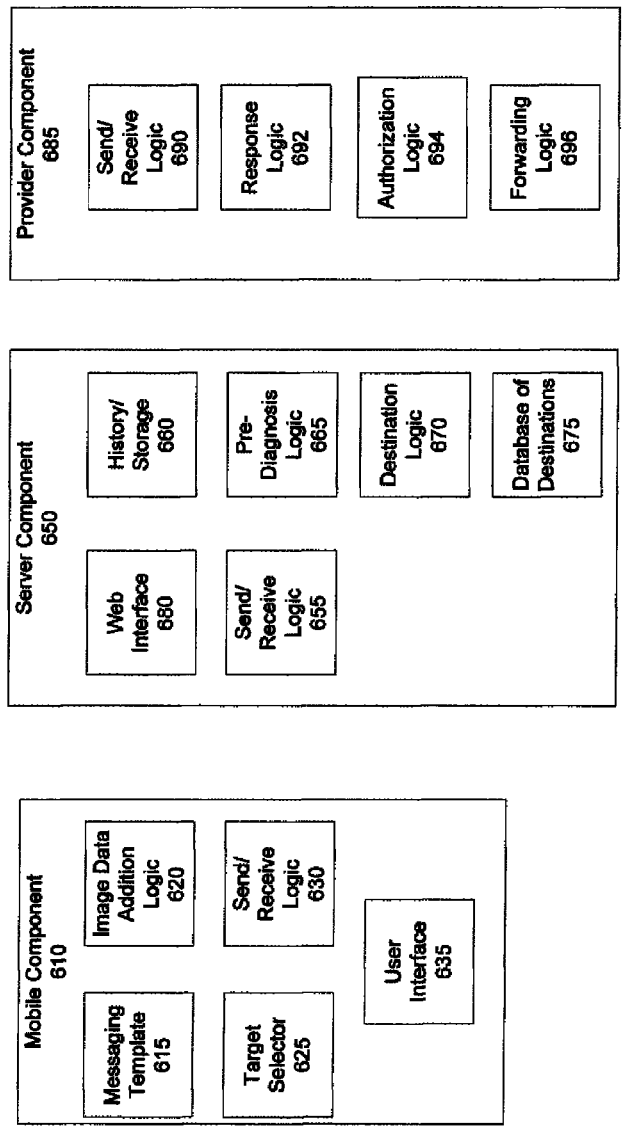
FIG. 6 is a block diagram of one embodiment of the messaging system.

FIG. 6 is a block diagram of one embodiment of the system which enables telemedicine through messaging. The system, in one embodiment, may include three components: a mobile component 610, a server component 650, and a provider component 685. The mobile component may be any mobile device which permits a user to send messages. For example, a cellular telephone device may have the mobile component 610. The server component 650 may be any system which is coupled to the historical database 660, which may be part of the SIMS system.

The mobile component 610, in one embodiment, includes a send/receive logic 630. The send/receive logic 630 enables the mobile component 610 to send the messages to the server component 650, and or the provider component 685. In one embodiment, any messages sent to the provider component 685 are automatically copied to the server component 650, so that a full record may be maintained in the historical database 660. In one embodiment, the provider component 685 automatically sends any messages received from mobile components 610 to the server component 650.

In one embodiment, the mobile component 610 includes a user interface 635 to enable the user to construct telemedicine messages, and receive responses. In one embodiment, for the creation of the messages, the user may utilize one or more messaging templates 615. The messaging templates 615 enable the user to create messages for the telemedicine system. The messaging templates 615, in one embodiment, include the destination address, a title/tag area to permit the user to label the message, and a space for any images or other non-text data. The user can add images to the message using image data addition logic 620. In one embodiment, target selector 625 enables the user to select one or more recipients for the message. In one embodiment, the default destination for messages is the server component 650. In one embodiment, the user may send the message to any authorized provider. In one embodiment, regardless of which individual provider is selected as the target, the message is routed through server component 650.

In one embodiment, these components may be part of the standard elements in the mobile device, for example the messaging service of a cellular telephone. Thus, in one embodiment, an existing mobile device need not be modified, or have any applications installed in order to be used for this purpose. Simply by providing a template (or merely a destination address), the system can be used for the telemedicine system described herein.

The server component 650 may reside on the multimedia messaging service center (MMSC) on the cellular network. Alternatively, the server component 650 may be a destination unrelated to the MMSC.

In one embodiment, send/receive logic 655 in server component 650 receives messages from mobile component 610. In one embodiment, the user may also construct messages using a web interface 680. All queries, in one embodiment, whether received via send/receive logic 655 or web interface 680 are stored in history 660. History 660 also stores responses, and any other associated data. In one embodiment, history 660 may be part of the historical SMD database 230, shown in FIG. 2.

Returning to FIG. 6, in one embodiment, the server component 650 includes a pre-diagnosis logic 665, The pre-diagnosis logic 665 analyzes the message, and identifies a target provider for the message. In one embodiment, pre-diagnosis logic also attaches an analysis of the problem, and a potential solution to the message, prior to forwarding it to a practitioner. In one embodiment, pre-diagnosis logic 665 creates a response which is sent to the user. In one embodiment, this is only the case for situations in which the diagnosis is certain. In one embodiment, the only response that pre-diagnosis logic 665 may return directly to the user is a warning that the condition appears to be sufficiently dangerous that the user should visit an emergency room immediately.

Destination logic 670 selects the provider to whom the message should be forwarded. In one embodiment, destination logic 670 makes this determination based on the identity of the user whose condition is being analyzed, and the content of the message. For example, a user may have an insurance provider, which has authorized contact persons. The combination of the condition (i.e. chickenpox) and insurance (i.e. HMO provided by Company X) identifies a designated provider (i.e. a pediatrician designated by Company X). The provider information is determined based on the database of destinations 675. The server component 650 the forwards the message to the appropriate destination. In one embodiment, the server component 650 notifies the user that the message has been passed on.

Provider component 685 receives the message either directly from the mobile component 610 or from server component 650. In one embodiment, if the message is received directly from the mobile component 610, the send/receive logic 690 in provider component 685 sends a copy to the server component 650.

The recipient can then formulate a response, utilizing response logic 692. In one embodiment, response logic 692 may be a conventional message creation application, such as an email application. In one embodiment, the provider component 685 may also be on a mobile device, and the response logic 692 may be a multimedia messaging component to construct MMS messages.

In one embodiment, provider component 685 includes an authorization logic 694, which enables the provider to authorize the message to be forwarded to a specialist. This is useful, for example, in an HMO situation, where a primary care physician must review issues prior to consulting a specialist. In one embodiment, the provider can forward the message directly to the specialist, using forwarding logic 696. In one embodiment, forwarding logic 696 may have access to the database of destinations 675 on server component 650. In another embodiment, the provider component 685 may have access to a separate database of destinations, either locally or remotely.

Note that while this figure illustrates each of these components as unitary devices, the functionality described herein may be divided differently. For example, databases may be located remotely from the server component 650, or provider component 685. The target selector 625 may actually be accessing data external to the mobile component, etc. Therefore, the positioning of these logics within the figure should not be taken as restrictive.

Figure 3:
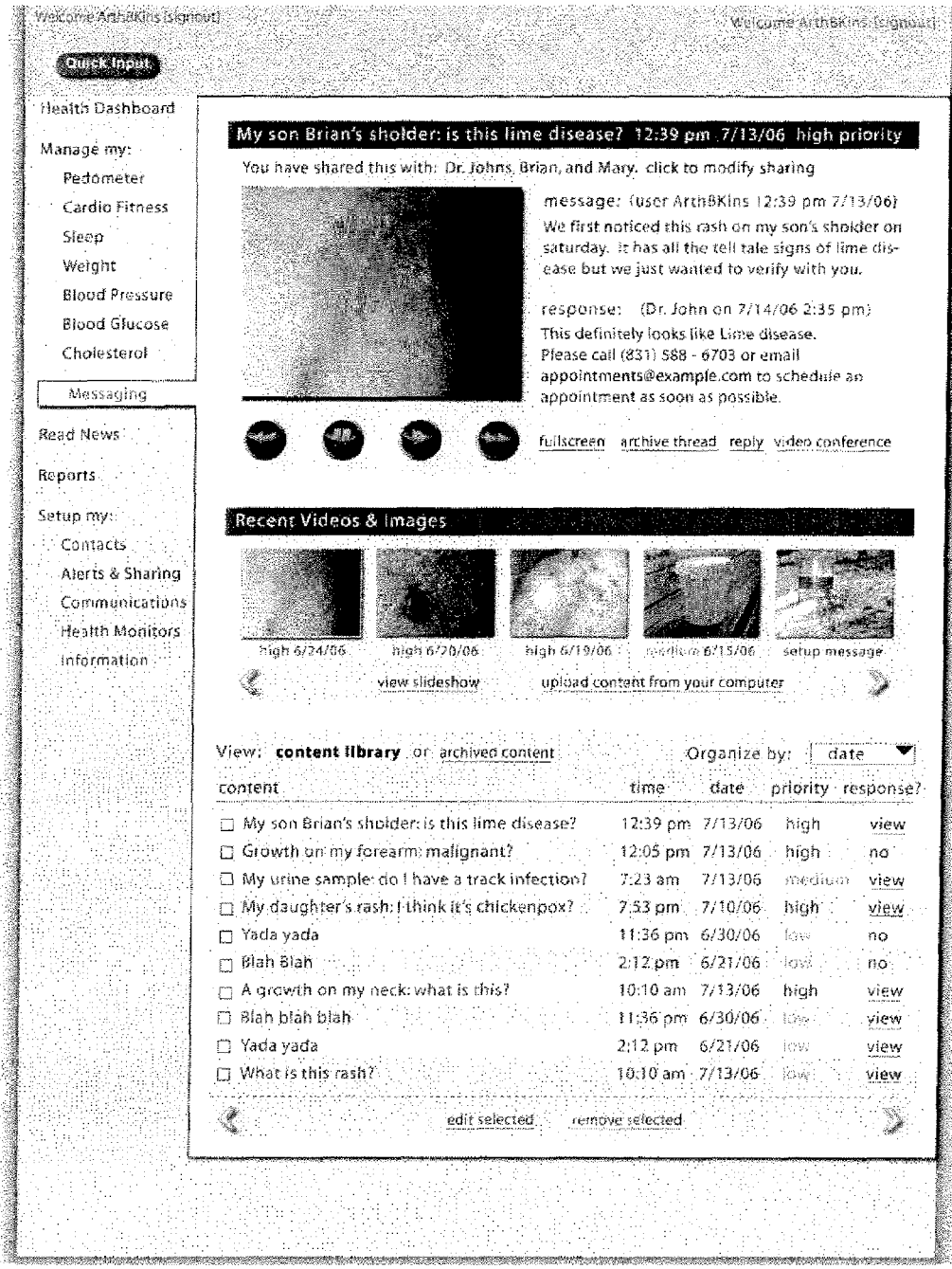
FIG. 3 is an exemplary messaging center which lists messages.

FIG. 3 is an exemplary messaging center which lists messages. As can be seen, in this example, the messages may be accessible through a web interface. The messages listed include past messages sent, and their priorities.

In one embodiment, the central database in the SIMS collects these messages. In one embodiment, these messages are routed through the SIMS, and forwarded by the SIMS to the appropriate target. In one embodiment, the SIMS automatically provides routing. For example, a user may send a message to the SIMS via a handheld device such as a cell phone. The message may include one or more descriptive terms (for example "Lyme disease," "mole," "chickenpox" and similar terms. These terms may be identified, as tags attached to the message, or may be part of the title or message body. Based on these terms, in one embodiment the SIMS automatically routes the message to an appropriate practitioner. In one embodiment, additional data about the patient known by the system, may be used to correctly route the message. In one embodiment, the message may be routed to the appropriate medical provider (i.e. a doctor specializing in Lyme disease, a dermatologist, and a pediatrician, respectfully in the above example.) But, for example, if the patient inquiring about chickenpox is a pregnant woman, the message may instead be routed to an obstetrician. In another embodiment, an expert system within the SIMS may make a preliminary diagnosis based on the data and description provided, and in one embodiment additional available data from the SIMS system.

In one embodiment, the SIMS, or the medical provider, may respond to the query. As can be seen in FIG. 3, the responses are viewable as well, and the user can quickly determine whether a particular query has a response. In one embodiment, the SIMS stores the responses as well.

In one embodiment, the entire exchange, including any follow-up messages are stored. This historical data may be very useful (for example indications that the user has had chickenpox may be useful in other diagnoses). Furthermore, in one embodiment, the responsiveness of patients as well as medical providers can be easily evaluated based on this data.

In one embodiment, the medical provider's response is directed through the SIMS as well, which forwards it to the appropriate user. In one embodiment, the user may set preferences for a response. For example, a user may ask for a response via email, SMS, telephone, fax, or other means. In one embodiment, the SIMS system may be able to translate a response to any one of these formats, and provide the response to the user. In particular, the SIMS system may convert text to speech, or vice versa, in order to provide the response in the format requested by the user. In one embodiment, similar format changes may be made in transmitting the original query to the appropriate provider.

Figure 4:
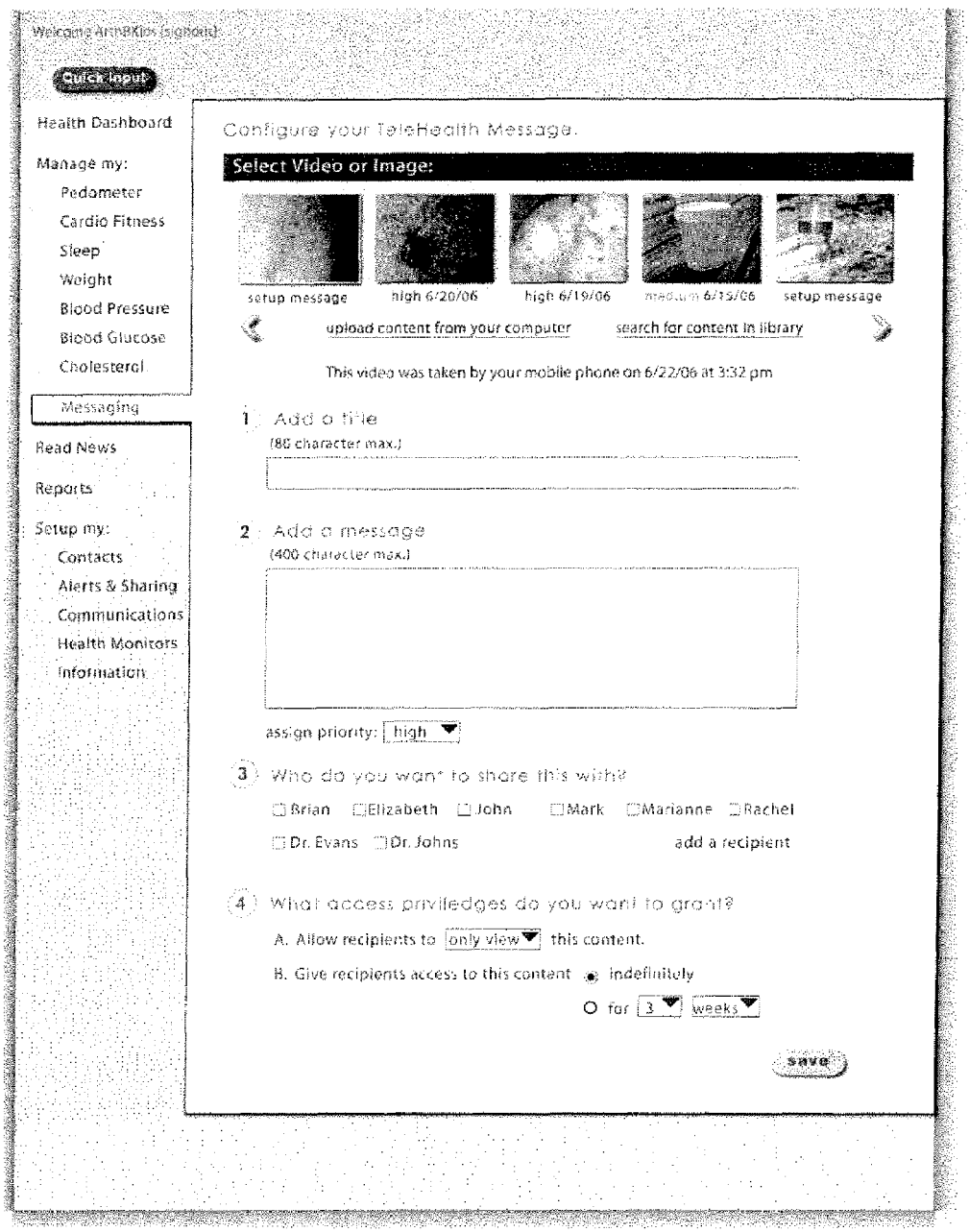
FIG. 4 is an exemplary message that may be sent by a user.

FIG. 4 is an exemplary message that may be sent by a user. The user may select a title, enter a message, select priority, and select a destination. In one embodiment, one additional destination may be an "appropriate medical personnel" option. If the user does not know which doctor to direct a particular query-to, the SIMS system may, based on the message and data content, route the message. In one embodiment, the service may be provided through the user's insurance provider (Le. HMO, PPO, etc.) In that instance, in one embodiment, the routing may be defined by the user's insurance provider. In one embodiment, if the user has an HMO, the available providers' identities may be listed for the user's selection. For example, the user may be required to contact his or her primary care physician, who can then refer the user to another provider. In that instance, in one embodiment, initial queries can only be directed to the primary care physician. However, in one embodiment, the primary care physician may respond with an authorization to contact the appropriate specialist, or may directly forward the query to the appropriate specialist. In one embodiment, for some health care providers, the user's initial query goes to an authorized individual, group, or entity that is not a medical professional—i.e. an insurance company employee, a nurse practitioner, or another appropriate personnel. The original recipient can, in one embodiment, forward the query as appropriate based on the content and the health care status of the user.

In one embodiment, the user may also determine access to the message. For example, the access may be limited to a particular time-frame. Thus, for example, the user may send a query "for response within 3 days." If no response is received within 3 days, the user may be alerted to this. In one embodiment, the message is then removed from the responder's queue. This may be appropriate, for example, if a user has a scheduled doctor's visit at some point, and wishes to receive data prior to that visit. Thus, if the response is not received prior to the visit, it may be aged out, and therefore no longer relevant.

Figure 5:
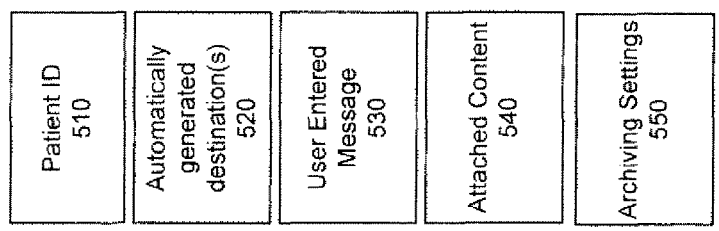
FIG. 5 is an exemplary messaging layout.

FIG. 5 is an exemplary messaging layout. In one embodiment, the messaging layout may be in a template that the user may have on their mobile system. In one embodiment, the messaging layout may be a template on a web site or other user-accessible system.

The messaging layout may include an automatically assigned patient ID 510. As noted above, the patient ID may not match the patient ID used by the hospital or other provider. Rather, the SIMS system may use a hash or other obscuring mechanism, or a random number for patient ID. In one embodiment, a unique ID assigned to each message, which enables the doctor to obtain data about the patient, but disassociates the patient from the message.

The message may further include an automatically generated destination. In one embodiment, the cc: field may be automatically generated while the user may edit the to: field. The automatically generated destination, in one embodiment, is the SIMS system (which then provides centralized storage for the data). In one embodiment, the user may further select another automatically generated destination—either globally or on a per message basis. The other automatically generated destination routes the message to the appropriate medical provider. For example, the patient may not have a doctor, and so may direct the message to Kaiser or a similar global provider. In one embodiment, the SIMS system, based on the message 530 and content 540, may route the message to the appropriate individual or department. In one embodiment, the telemedicine system may provide dedicated nurses, doctors, expert systems, or combinations of the above, to analyze user messages. In that instance, the user never needs to enter a destination. Rather, the automatically generated destination 520 provides the routing to the dedicated providers.

As noted above, in one embodiment, additional media data may be included. The media data may include images, video, recordings, attached data of any sort. For example, the user may send readings from their medical device as an attachment.

In one embodiment, the message may further include archiving settings 550. Archiving settings 550 determine whether, and how long, the data may be stored. In one embodiment, the user may set limits to archiving within the SIMS system. In another embodiment, the user may not control the SIMS archiving, but may control archiving on the medical providers' systems. In one embodiment, archiving settings may range from "until responded to" or "an hour" to "forever." In one embodiment, the default setting is to permit permanent archiving.

Telemedicine is especially useful in pre-diagnosis. For example, in determining whether a mole could be cancerous, whether a tick bite may be Lyme disease, whether a particular stool sample is indicative of some problem, whether a cough may be whooping cough. Especially for suddenly appearing symptoms, the ability to immediately take a picture/recording/video or other permanent record is extremely useful. Furthermore, a nurse or doctor can make a preliminary diagnosis, and either prompt the user to go to the doctor immediately, or remove/reduce concern. This would be particularly useful for diagnosis of unusual conditions (as the doctor would be able to share the data with specialists immediately), for users living far away from medical care, for short-lived symptoms, and for symptoms that may make it difficult to drive to the doctor (such as eye problems for someone who does not have a driver available).

Figure 7:
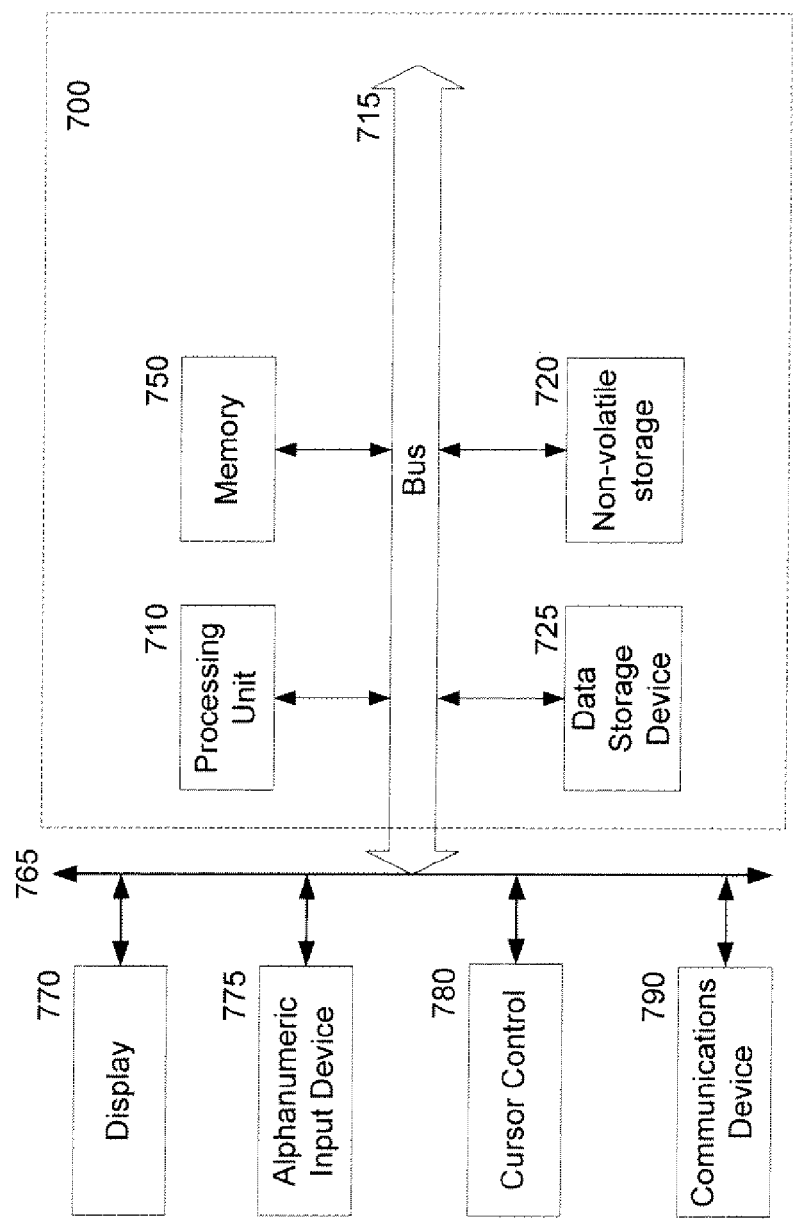
FIG. 7 is a block diagram of one embodiment of a computer system which may be used with the present invention.

FIG. 7 is one embodiment of a computer system that may be used with the present invention. It will be apparent to those of ordinary skill in the art, however that other alternative systems of various system architectures may also be used.

The data processing system illustrated in FIG. 7 includes a bus or other internal communication means 715 for communicating information, and a processor 710 coupled to the bus 715 for processing information. The system further comprises a random access memory (RAM) or other volatile storage device 750 (referred to as memory), coupled to bus 715 for storing information and instructions to be executed by processor 710. Main memory 750 also may be used for storing temporary variables or other intermediate information during execution of instructions by processor 710. The system also comprises a read only memory (ROM) and/or static storage device 720 coupled to bus 715 for storing static information and instructions for processor 710, and a data storage device 725 such as a magnetic disk or optical disk and its corresponding disk drive. Data storage device 725 is coupled to bus 715 for storing information and instructions.

The system may further be coupled to a display device 770, such as a cathode ray tube (CRT) or a liquid crystal display (LCD) coupled to bus 715 through bus 765 for displaying information to a computer user. An alphanumeric input device 775, including alphanumeric and other keys, may also be coupled to bus 715 through bus 765 for communicating information and command selections to processor 710. An additional user input device is cursor control device 780, such as a mouse, a trackball, stylus, or cursor direction keys coupled to bus 715 through bus 765 for communicating direction information and command selections to processor 710, and for controlling cursor movement on display device 770.

Another device, which may optionally be coupled to computer system 700, is a communication device 790 for accessing other nodes of a distributed system via a network. The communication device 790 may include any of a number of commercially available networking peripheral devices such as those used for coupling to an Ethernet, token ring, Internet, or wide area network. The communication device 790 may further be a null-modem connection, or any other mechanism that provides connectivity between the computer system 700 and the outside world. Note that any or all of the components of this system illustrated in FIG. 7 and associated hardware may be used in various embodiments of the present invention.

It will be appreciated by those of ordinary skill in the art that any configuration of the system may be used for various purposes according to the particular implementation. The control logic or software implementing the present invention can be stored in main memory 750, mass storage device 725, or other storage medium locally or remotely accessible to processor 710.

It will be apparent to those of ordinary skill in the art that the system, method, and process described herein can be implemented as software stored in main memory 750 or read only memory 720 and executed by processor 710. This control logic or software may also be resident on an article of manufacture comprising a computer readable medium having computer readable program code embodied therein and being readable by the mass storage device 725 and for causing the processor 710 to operate in accordance with the methods and teachings herein.

The present invention may also be embodied in a handheld or portable device containing a subset of the computer hardware components described above. For example, the handheld device may be configured to contain only the bus 715, the processor 710, and memory 750 and/or 725. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processor 710, a data storage device 725, a bus 715, and memory 750, and only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism.

It will be appreciated by those of ordinary skill in the art that any configuration of the system may be used for various purposes according to the particular implementation. The control logic or software implementing the present invention can be stored on any machine-readable medium locally or remotely accessible to processor 710. A machine-readable medium includes any mechanism for storing or transmitting information in a form readable by a machine (e.g. a computer). For example, a machine readable medium includes read-only memory (ROM), random access memory (RAM), magnetic disk storage media, optical storage media, flash memory devices, electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A telemedicine system comprising:
   user interface provided to a non-expert user to initiate an interaction, the interface to receive a telemedicine query from the non-expert user regarding a concerning medical condition of a patient, the telemedicine query including a question and health data in the form of media data attached by the non-expert user to the telemedicine query in connection with the question, the telemedicine query requesting a preliminary remote diagnosis of the concerning medical condition before the patient is physically examined by a medical practitioner;
   a server comprising a processor configured to automatically determine an appropriate responder from a plurality of responders based on one or more of: the media data in the telemedicine query, text in the telemedicine query, and data of the patient, wherein the appropriate responder and the medical practitioner are different entities;

the processor, before the patient is physically examined by the medical practitioner, to:
target the telemedicine query to the appropriate responder to create the preliminary remote diagnosis to the telemedicine query,
forward the telemedicine query to the appropriate responder,
receive the preliminary diagnosis from the appropriate responder, and present the preliminary remote diagnosis to the user;

a memory to maintain a history of data exchanges between the non-expert user and one or more responders of the plurality of responders,
the history of data exchanges including the telemedicine query including the question and the media data attached by the non-expert user,
the history including follow-up messages and the preliminary remote diagnosis received from the appropriate responder,
the history reflecting concerns of the non-expert user over time,
wherein the history is provided to the medical practitioner to enable the medical practitioner to evaluate the concerning medical condition in view of the history of data exchanges, and
the history of any prior exchanges is also available to the responder when creating the preliminary diagnosis.

2. The system of claim 1, wherein the user interface is utilized to present the preliminary diagnosis to the non-expert user, wherein the user interface is a web interface to enable the non-expert user to generate the telemedicine query.

3. The system of claim 2, wherein the user interface is a mobile interface accessible through a mobile telephone.

4. The system of claim 1, further comprising:
a pre-diagnosis logic to identify the media data in the telemedicine query used to select the appropriate responder.

5. The system of claim 1, wherein the data of the patient used to determine the appropriate responder comprises one or more of the following of the patient's: gender, age, health status, and insurance provider.

6. The system of claim 1, further comprising: a mobile component utilized by the non-expert user, a server component to target the telemedicine query and maintain the history, and a provider component to enable an appropriate responder to respond to the telemedicine query.

7. The system of claim 6, wherein the mobile component comprises a standard mobile telephone.

8. The system of claim 7, wherein the mobile component further includes one or more templates to enable formulation of the telemedicine query.

9. The system of claim 7, wherein the telemedicine query includes a messaging template including a destination address for the telemedicine query, and does not utilize a special application to enable the telemedicine system.

10. The system of claim 6, wherein the provider component comprises a standard computer system and does not require a special application.

11. The system of claim 1, further comprising:
an authorization logic which enables the appropriate responder to redirect the telemedicine query to another responder of the plurality of responders to create the preliminary remote diagnosis.

12. The system of claim 1, wherein the user interface permits the non-expert user to assign a priority to the telemedicine query.

13. The system of claim 1, wherein the non-expert user is the patient.

14. The system of claim 1, wherein the processor is further:
to determine the appropriate responder from the plurality of responders based on an insurance provider of the patient.

15. The system of claim 1, wherein the processor uses all available data of the media data in the telemedicine query, text in the telemedicine query, and the data of the patient to select the appropriate responder.

16. A method of providing a telemedicine system comprising:
enabling a non-expert user to construct a telemedicine query, the telemedicine query requesting a preliminary remote diagnosis of a concerning medical condition of a patient, the preliminary remote diagnosis rendered before a medical practitioner physically examines the patient;
receiving the telemedicine query by a server, the telemedicine query including a question and health data in the form of media data attached by the non-expert user to the telemedicine query in connection with the question;
automatically determining an appropriate responder from a plurality of responders based on one or more of: the media data in the telemedicine query, text in the telemedicine query, and data of the patient, wherein the appropriate responder and the medical practitioner are different entities;
before the patient is physically examined by the medical practitioner:
targeting the telemedicine query to the appropriate responder to create the preliminary remote diagnosis to the telemedicine query;
forwarding the telemedicine query to the appropriate responder by the server;
receiving the preliminary remote diagnosis from the appropriate responder by the server;
presenting the preliminary remote diagnosis to the user; and
maintaining a history of data exchanges between the non-expert user and one or more responders of the plurality of responders,
the history of data exchanges including the telemedicine query including the question and the media data attached by the non-expert user,
the history including follow-up messages and the preliminary remote diagnosis received from the appropriate responder,
the history reflecting concerns of the non-expert user over time,
wherein the history is provided to the medical practitioner to enable the medical practitioner to evaluate the concerning medical condition in view of the history of data exchanges, and
the history of any prior exchanges is also available to the responder when creating the preliminary diagnosis.

17. The method of claim 16, further comprising:
providing a template to enable the non-expert user to construct the telemedicine query.

18. The method of claim 16, wherein determining the appropriate responder further comprises:
using a user characteristic to identify the appropriate responder.

19. The method of claim 16, wherein the data of the patient comprises one or more of the following of the patient's: gender, age, health status, and insurance provider.

20. The method of claim 16, further comprising:
enabling the appropriate responder to redirect the telemedicine query to an other responder of the plurality of responders to create the preliminary remote diagnosis.

21. The method of claim 16, wherein determining an appropriate responder from a plurality of responders comprises:
determining the appropriate responder from the plurality of responders based on an insurance provider of the patient.

22. A non-transitory computer readable medium comprising instructions, that when executed by a processor, cause the processor to:
enable a non-expert user to construct a telemedicine query, the telemedicine query requesting a preliminary remote diagnosis of a concerning medical condition of a patient, the preliminary remote diagnosis rendered before a medical practitioner physically examines the patient;
receive the telemedicine query by a server, the telemedicine query including a question and health data in the form of media data attached by the non-expert user to the telemedicine query in connection with the question;
automatically determine an appropriate responder from a plurality of responders based on one or more of: the media data in the telemedicine query, text in the telemedicine query, and data of the patient, wherein the appropriate responder and the medical practitioner are different entities;
before the patient is physically examined by the medical practitioner:
target the telemedicine query to the appropriate responder to create the preliminary remote diagnosis to the telemedicine query;
forward the telemedicine query to the appropriate responder by the server;
receive the preliminary remote diagnosis from the appropriate responder by the server;
present the preliminary remote diagnosis to the user; and
maintain a history of data exchanges between the non-expert user and one or more responders of the plurality of responders,
the history of data exchanges including the telemedicine query including the question and the media data attached by the non-expert user,
the history including follow-up messages and the preliminary remote diagnosis received from the appropriate responder,
the history reflecting concerns of the non-expert user over time,
wherein the history is provided to the medical practitioner to enable the medical practitioner to evaluate the concerning medical condition in view of the history of data exchanges, and
the history of any prior exchanges is also available to the responder when creating the preliminary diagnosis.

23. The non-transitory computer readable medium of claim 22, wherein the data of the patient comprises one or more of the following of the patient's: gender, age, health status, and insurance provider.

24. The non-transitory computer readable medium of claim 22, further comprising:
enabling the appropriate responder to redirect the telemedicine query to another responder of the plurality of responders to create the preliminary remote diagnosis.

* * * * *